(12) United States Patent
Veneman et al.

(10) Patent No.: US 10,800,731 B2
(45) Date of Patent: Oct. 13, 2020

(54) PROCESS TO PREPARE HIGHER ETHYLENE AMINES OR UREA DERIVATIVES THEREOF

(71) Applicant: NOURYON CHEMICALS INTERNATIONAL B.V., Arnhem (NL)

(72) Inventors: Rens Veneman, Deventer (NL); Antoon Jacob Berend Ten Kate, Arnhem (NL); Michiel Jozef Thomas Raaijmakers, Deventer (NL); Eike Nicolas Kantzer, Uddevalla (SE); Rolf Krister Edvinsson, Partille (SE); Karl Fredrik Lake, Södertälje (SE); Ina Ehlers, Ödsmål (SE); Slavisa Jovic, Utrecht (NL); Hendrik Van Dam, Frölunda (SE); Lars Torbjörn Hagberg, Stockholm (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/630,293

(22) PCT Filed: Jul. 3, 2018

(86) PCT No.: PCT/EP2018/067869
§ 371 (c)(1),
(2) Date: Jan. 10, 2020

(87) PCT Pub. No.: WO2019/011711
PCT Pub. Date: Jan. 17, 2019

(65) Prior Publication Data
US 2020/0207701 A1 Jul. 2, 2020

(30) Foreign Application Priority Data

Jul. 10, 2017 (EP) .................................. 17180573

(51) Int. Cl.
| C07C 209/00 | (2006.01) |
| C07C 211/00 | (2006.01) |
| C07C 209/16 | (2006.01) |
| C07D 263/20 | (2006.01) |
| C07D 233/36 | (2006.01) |
| C07C 211/14 | (2006.01) |

(52) U.S. Cl.
CPC .......... C07C 209/16 (2013.01); C07C 211/14 (2013.01); C07D 233/36 (2013.01); C07D 263/20 (2013.01)

(58) Field of Classification Search
CPC .................. C07C 209/16; C07C 211/14
See application file for complete search history.

(56) References Cited

U.S. PATENT DOCUMENTS

| 2,812,333 | A | 11/1957 | Steele |
| 3,133,932 | A | 5/1964 | Horn et al. |
| 4,387,249 | A | 6/1983 | Harnden et al. |
| 4,503,250 | A | 3/1985 | Herdle |
| 4,568,745 | A | 2/1986 | Ghelli et al. |
| 5,262,534 | A | 11/1993 | King |
| 5,364,971 | A | 11/1994 | Su |
| 5,491,263 | A | 2/1996 | Rooney et al. |
| 2007/0100144 | A1 | 5/2007 | Frauenkron et al. |
| 2010/0029976 | A1 | 2/2010 | Dahmen et al. |
| 2010/0087681 | A1 | 4/2010 | Petraitis et al. |
| 2010/0087683 | A1 | 4/2010 | Cook et al. |

(Continued)

FOREIGN PATENT DOCUMENTS

| EP | 0222934 A1 | 5/1987 |
| EP | 1654214 B1 | 3/2007 |
| EP | 2548869 A1 | 1/2013 |

(Continued)

OTHER PUBLICATIONS

ISA, European Patent Office, International Search Report and Written Opinion issued in International Application No. PCT/EP2018/067866, dated Sep. 14, 2018.

(Continued)

Primary Examiner — Sikarl A Witherspoon
(74) Attorney, Agent, or Firm — Lorenz & Kopf, LLP

(57) ABSTRACT

A process is provided for preparing ethylene amines of the formula $NH_2—(C_2H_4—NH—)_pH$ wherein p is at least 2, or derivatives thereof wherein one or more units $—NH—C_2H_4—NH—$ are present as a cyclic ethylene urea unit

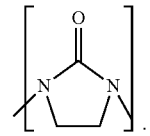

The process includes reacting an ethanolamine-functional compound $OH—(C_2H_4—NH—)_qH$ or $HO—(C_2H_4—NH)_q—C_2H_4—OH$ wherein q is at least 1, and an amine-functional compound $NH_2—(C_2H_4—NH—)_rH$ wherein r is at least 1, in the presence of a carbon oxide delivering agent and water, with a molar ratio of water:carbon oxide delivering agent of from about 0.01:1 to about 2:1.

11 Claims, No Drawings

(56) References Cited

U.S. PATENT DOCUMENTS

2010/0120983 A1    5/2010    Dufaure et al.

FOREIGN PATENT DOCUMENTS

| | | |
|---|---|---|
| FR | 2912148 | 8/2008 |
| GB | 1510538 | 5/1978 |
| WO | 9749686 A1 | 12/1997 |
| WO | 2011079008 A1 | 6/2011 |
| WO | 2011107512 A1 | 9/2011 |
| WO | 2017137529 A1 | 8/2017 |
| WO | 2017137530 A1 | 8/2017 |
| WO | 2017137532 A1 | 8/2017 |

OTHER PUBLICATIONS

ISA, European Patent Office, International Search Report and Written Opinion issued in International Application No. PCT/EP2018/067867, dated Aug. 20, 2018.
ISA, European Patent Office, International Search Report and Written Opinion issued in International Application No. PCT/EP2018/067868, dated Oct. 1, 2018.
ISA, European Patent Office, International Search Report and Written Opinion issued in International Application No. PCT/EP2018/067869, dated Sep. 14, 2018.
EPO, European Extended Search Report issued in European Patent Application No. 17180568.2, dated Oct. 13, 2017.
EPO, European Extended Search Report issued in European Patent Application No. 17180569.0, dated Jan. 22, 2018.
EPO, European Extended Search Report issued in European Patent Application No. 17180571.6, dated Jan. 22, 2018.
EPO, European Extended Search Report issued in European Patent Application No. 17180573.2, dated Jan. 22, 2018.

PROCESS TO PREPARE HIGHER ETHYLENE AMINES OR UREA DERIVATIVES THEREOF

CROSS-REFERENCE TO RELATED APPLICATION

This application is a U.S. National-Stage entry under 35 U.S.C. § 371 based on International Application No. PCT/EP2018/067869, filed Jul. 3, 2018, which was published under PCT Article 21(2) and which claims priority to European Application No. 17180573.2, filed Jul. 10, 2017, which are all hereby incorporated in their entirety by reference.

TECHNICAL FIELD

The present invention relates to a process to prepare higher ethylene amines by reacting an amine-functional compound with an ethanolamine-functional compound in the presence of a carbon oxide delivering agent.

BACKGROUND

Ethylene amines consist of two or more nitrogen atoms linked by ethylene units. Ethylene amines can be present in the form of linear chains $H_2N(-C_2H_4NH)_p-H$. For p=1, 2, 3, 4, . . . these are denoted EDA, DETA, L-TETA, L-TEPA, . . . .

With three or more ethylene units it is also possible to create branched ethylene amines such as $N(CH_2CH_2NH_2)_3$, TAEA. Two adjacent nitrogen atoms linked by two ethylene units are called a piperazine ring

Piperazine rings can be present in longer chains to produce the corresponding cyclic ethylene amines.

Two adjacent nitrogen atoms linked by one ethylene unit and one carbonyl moiety form a cyclic ethylene urea (EU). An ethylene amine (EA) in which two nitrogen atoms are linked intramolecular by a carbonyl moiety

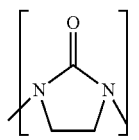

is here referred to as an UEA. Replacing the carbonyl bridge with two hydrogen atoms yields the corresponding ethylene amine. For example: EU↔EDA, UDETA↔DETA, UAEEA↔AEEA, UTETA↔L-TETA, UTEPA↔L-TEPA. Some higher amines host more than one carbonyl moiety, e.g. DUTETA the diurea of L-TETA. The carbonyl moiety may link nitrogen atoms on two separate molecules. For example $H_2NC_2H_4NH-CO-NHC_2H_4NH_2$ and replacing the carbonyl moiety with two hydrogen atoms here yields two EDA.

Each amine function in ethylene amines and ethylene ureas can be primary, secondary or tertiary. Furthermore, a secondary amine can be linear (linear secondary amines, LSA) or cyclic (cyclic secondary amine, CSA).

In the presence of any Brønsted acid (such as water) ethylene amines (EA) can be protonated (EAH$^+$). If not otherwise stated the term amine in this document will include both the protonated and unprotonated form.

Some ethylene amines and urea derivatives thereof are shown below as an illustration. This can naturally be extended to include a.o. pentaamines, hexaamines and so on.

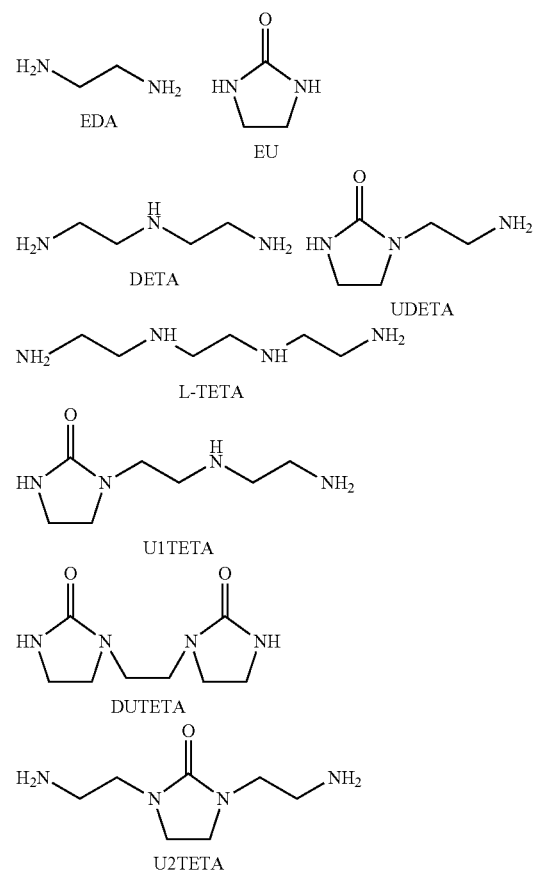

As to naming of the molecules, EDA stands for ethylenediamine, DETA for diethylenetriamine, TETA for triethylenetetraamine, TEPA for tetraethylenepentamine, PEHA for pentaethylenehexamine (L-TETA, L-TEPA and L-PEHA when specifically referring to the linear version of TETA, TEPA and PEHA as in the above drawings). When there is a single cyclic urea in the molecule this is indicated by adding a U in front of the name, i.e. UTETA means the cyclic urea of TETA, while when there are two cyclic ureas in the molecule this is indicated by DU, i.e. DUTETA means the internal cyclic diurea of TETA. If there is a number indicated for the U this refers to the amino group where the U group is located. There is one exception to this naming and that is that instead of UEDA the abbreviation EU is used, which stands for ethyleneurea. An alkylene amine oftentimes exists in a mixture of isomers such as for TETA: L-TETA, TAEA, DAEP, and PEEDA.

The manufacturing of ethylene amines is presently dominated by two routes. These are the reductive amination of MEA and the EDC route.

Reductive amination of MEA proceeds in the presence of a hydrogenation/dehydrogenation catalyst in an excess of ammonia. Next to the reductive amination of MEA to give EDA a number of side reactions including transamination produce a mixture of a large number of ethylene and ethanolamines. The output is dominated by mono and diethylene products (EDA, DETA, PIP and AEEA). Higher ethylene and ethanolamines are also formed but the mixture is complex and ineffective in producing high yields of the most important higher ethylene amines TETA and TEPA.

Several attempts to use transamination to produce ethylene amines with two or more ethylene units have been reported but seem limited to the diethylene compound DETA and have not been competitive to the EDC route described further below. See for example U.S. Pat. No. 8,383,860 B2; U.S. Pat. No. 8,188,318 B2; EP1654214B1 and U.S. Pat. No. 4,568,745.

The EDC route is the substitution reaction of EDC (ethylene dichloride) with ammonia and/or another ethylene amine at elevated temperatures and pressures to form hydrochlorides which are then reacted with caustic to generate mixtures of ethylene amines and NaCl.

Today, the EDC-based process is the main process for producing higher polyethylene polyamines By higher ethylene amines we refer to those containing three or more ethylene units. AEP is an example of a triamine. Higher amines usually exist in so-called technical mixtures. For example, there are several tetramines possible and their technical mixture which is referred to as TETA typically comprises L-TETA, TAEA, DAEP, PEEDA. Similarly TEPA refers to a mixture of pentaamines (linear, branched and piperazine containing).

The EDC route apart from it being fully dependent on the use of ethylene dichloride which is toxic, highly flammable and carcinogenic expensive, difficult to handle and therefore not always and everywhere available has as a disadvantage that it has a low selectivity towards specific higher ethylene amines, as it gives a mixture of many different polyethylene amines. Furthermore the EDC route results in the creation of a lot of NaCl which in embodiment results in corrosion and colored products thereby creating a need for additional purification steps like distillation or bleaching.

U.S. Pat. No. 4,503,250 discloses the preparation of linear triethylene tetraamine L-TETA by reacting aminoethylethanolamine (AEEA) with EDA and a carbonic acid derivative (i.e. a carbon oxide delivering agent) such as imidazolidinone (which is the same as ethylene urea). It is said that the carbonic acid derivative can be a compound formed by earlier addition of an amine or alcohol to carbon dioxide. In all examples during the reaction there is no water present in the reaction mixture as only the reactants were charged in a closed vessel.

It has now been found that the best balance between conversion and selectivity, and hence improved yield, of the process to the ethylene amines products can be obtained if there is water present during the reaction of the amine functional compound and the ethanolamine functional compound within a well-chosen molar amount.

BRIEF SUMMARY

A process is provided for preparing ethylene amines of the formula $NH_2-(C_2H_4-NH-)_pH$ wherein p is at least 2, or derivatives thereof wherein one or more units $-NH-C_2H_4-NH-$ are present as a cyclic ethylene urea unit

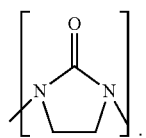

The process comprises reacting an ethanolamine-functional compound $OH-(C_2H_4-NH-)_qH$ or $HO-(C_2H_4-NH)_q-C_2H_4-OH$ wherein q is at least 1, and an amine-functional compound $NH_2-(C_2H_4-NH-)_rH$ wherein r is at least 1, in the presence of a carbon oxide delivering agent and water, with a molar ratio of water:carbon oxide delivering agent of from about 0.01:1 to about 2:1.

DETAILED DESCRIPTION

The present invention now provides a process to prepare ethylene amines of the formula $NH_2-(C_2H_4-NH-)_pH$ wherein p is at least 2, or derivatives thereof wherein one or more units $-NH-C_2H_4-NH-$ may be present as a cyclic ethylene urea unit

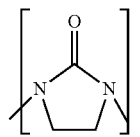

comprising the step of reacting an ethanolamine-functional compound $OH-(C_2H_4-NH-)_qH$ or $HO-(C_2H_4-NH)_q-C_2H_4-OH$ wherein q is at least 1, an amine-functional compound $NH_2-(C_2H_4-NH-)_rH$ wherein r is at least 1 in the presence of a carbon oxide delivering agent and water with a molar ratio of water:carbon oxide delivering agent of from 0.01:1 to 2:1.

It should be noted that U.S. Pat. No. 2,812,333 discloses a process for the preparation of 1-(2-hydroxyethyl)imidazolidine-2 (UAEEA) by reacting MEA with CO2. The document says that water as a solvent is preferred because it has low cost, there is ease of removal and high solvent power. In Example III of D3 traces of water are used which are undefined as to exact molar amount. In this Example III the yield of product is lower than with excess of water. Accordingly, on the basis of U.S. '333 there is no teaching or suggestion towards an optimum amount of water for a process involving a reaction of an ethanolamine-functional compound and an amine-functional compound in the presence of a carbon oxide delivering agent as in the present invention.

Preferably the ethanolamine-functional compound is of the formula compound OH—(C2H4-NH-)qH.

Preferably the molar ratio of water:carbon oxide delivering agent is between 0.05:1 and 1:1.

The molar amount of water is the molar amount of water as present when the reaction of the process is started.

In embodiments, additional water is formed during the process of the invention, which is not included in the above molar ratio.

In preferred embodiments however, the molar ratio of water:carbon oxide delivering agent is between 0.01:1 and 2:1, even more preferred between 0.05:1 and 1:1, not only initially but during the whole process.

The reaction mixture is characterized by containing as reactants ethanolamine-functional compound, amine-functional compound and carbon oxide delivering agent and can be roughly represented by below non-limiting scheme.

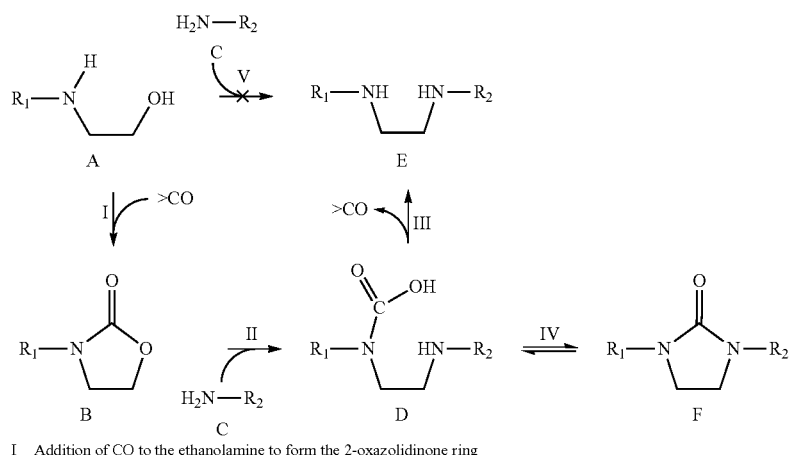

I   Addition of CO to the ethanolamine to form the 2-oxazolidinone ring
II  Chain extension by ring opening by primary amine
III Removal of carbonyl group to form the ethylene amine
IV  Intramolecular rearrangement of carbonyl group
V   Hypothetical direct uncatalyzed amination A number of reactions take place in parallel when heating a mixture of a carbonyl source, an ethanolamine-functional compound and an amine-functional compound.

Without being bound to theory this can be summarized in two main reaction steps each composed of multiple sub steps: 1) the activation of the alcohol function (A) by the carbonyl group, the oxazolidinone (B) is assumed to be an intermediate, 2) the activated alcohol function is replaced by an amine (C) to give a chain extended primary addition product (D). In the presence of ammonia a conversion of the alcohol function to an amine function without giving a chain extension can take place as well. The product (D) may undergo further reaction leading to secondary CO containing products as illustrated by reaction IV and product (F). Such products include but are not limited to cyclic ethylene urea derivatives but include all kinds of CO containing amines as for example illustrated in below examples of CO delivering agents. Optionally the CO groups can be removed leading to the formation of an ethylene amine (E).

The process of the invention can result in the formation of ethylene amines and/or derivatives of ethylene amines. These derivatives are defined as compounds that have the same structural formula as the ethylene amine, namely $NH_2—(C_2H_4—NH—)_pH$ wherein p is at least 2, with as a difference that one or more units $—NH—C_2H_4—NH—$ are present as a cyclic ethylene urea unit

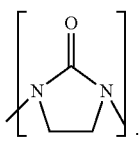

It is known to the skilled person that such derivatives can be hydrolyzed to give ethylene amines Such hydrolysis can for example be done by treatment with a basic solution such as aqueous sodium hydroxide, preferably under elevated temperatures of between 100 and 300 deg C. Such hydrolysis is also described in U.S. Pat. No. 4,503,250 where refluxing the reaction mixture overnight with 50 percent aqueous potassium hydroxide (8 moles KOH per mole of carbon oxide) is disclosed to give hydrolysis of the cyclic urea unit.

Accordingly, in an embodiment the reaction product of the process of the present invention comprising one or more compounds in the form of urea adducts is subjected to a CO removal reaction to convert the urea adduct into amine compounds.

It should be noted that the net reaction in the process of the present invention is the reaction of the ethanolamine-functional compound and the amine-functional compound to give a larger amine than the starting amine-functional compound. In embodiments wherein part of the products are urea adducts, the carbon oxide delivering agent is also a reactant, but if the product is free from such urea adducts, the carbon oxide delivering agent in the net reaction is not a reactant, unless this carbon oxide delivering agent is carbon oxide delivering agent and ethanolamine-functional compound or amine-functional compound at the same time.

The ethanolamine-functional compound is preferably a compound containing one hydroxyl group linked via an ethylene to an amine group that optionally may be present as its carbamate equivalent and the ethanolamine-functional compound is of the following formulae

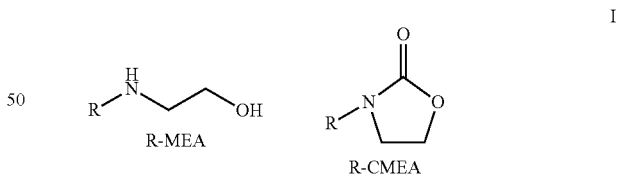

wherein R is a proton or an ethyleneamine group of the formula $—(C_2H_4—N)_{q-1}—H$ (q being at least 1 as defined above).

Examples of ethanolamine functional compounds include

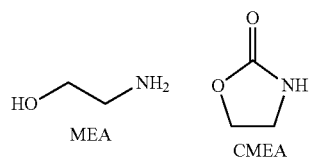

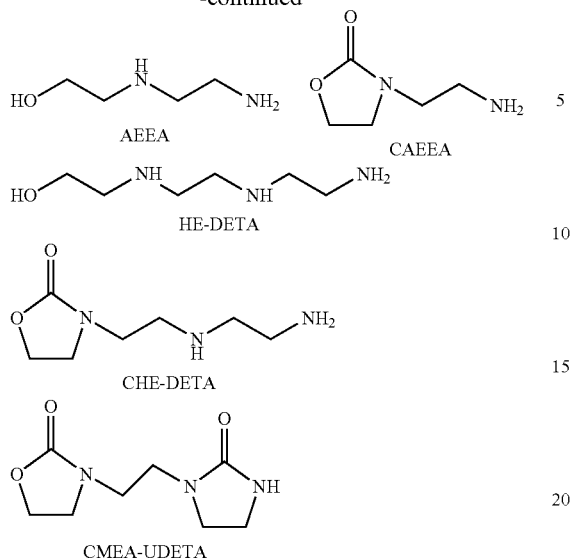

As to naming convention, MEA stands for monoethanolamine, AEEA stands for aminoethylethanolamine (also referred to as hydroxyethylethylenediamine), HE-DETA for hydroxyethyldiethylenetriamine, and from there on HE-TETA for hydroxyethyl triethylenetetramine etc. By using the letter C it is indicated that a cyclic carbamate ring is present in the molecule The carbon oxide delivering agent is a compound containing a carbonyl moiety that can be transferred to an ethanolamine functional compound leading to the formation of a cyclic carbamate, such as CMEA (the cyclic carbamate of monoethanolamine), or that can be transferred to an ethylene amine (EA) leading to the formation of the corresponding cyclic ethylene urea (UEA). Next to cyclic compounds linear carbamates and ureas may form as well.

Carbon oxide delivering agents within the scope of the present invention include organic compounds in which a carbonyl moiety is available for being transferred as described above. Organic compounds in which a carbonyl moiety is available for being transferred include carbon dioxide, urea, linear and cyclic alkylene ureas, especially cyclic ureas, mono or di-substituted alkylene ureas, alkyl and dialkyl ureas, linear and cyclic carbamates, especially cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate, bicarbonate or carbamate salts. Preferably the CO delivering agent is CO2, urea, or an organic compound wherein alkylene is ethylene, such as cyclic urea of an ethylene amine or an ethanolamine, ethylene carbonate, more preferably the carbon oxide delivering agent is at least partly added as carbon dioxide or urea. The carbon oxide delivering agent can be present in the process in the same molecule as the amine functional or the ethanolamine functional compound by using the aforementioned urea or carbamate compounds.

Examples of carbon oxide delivering agents include

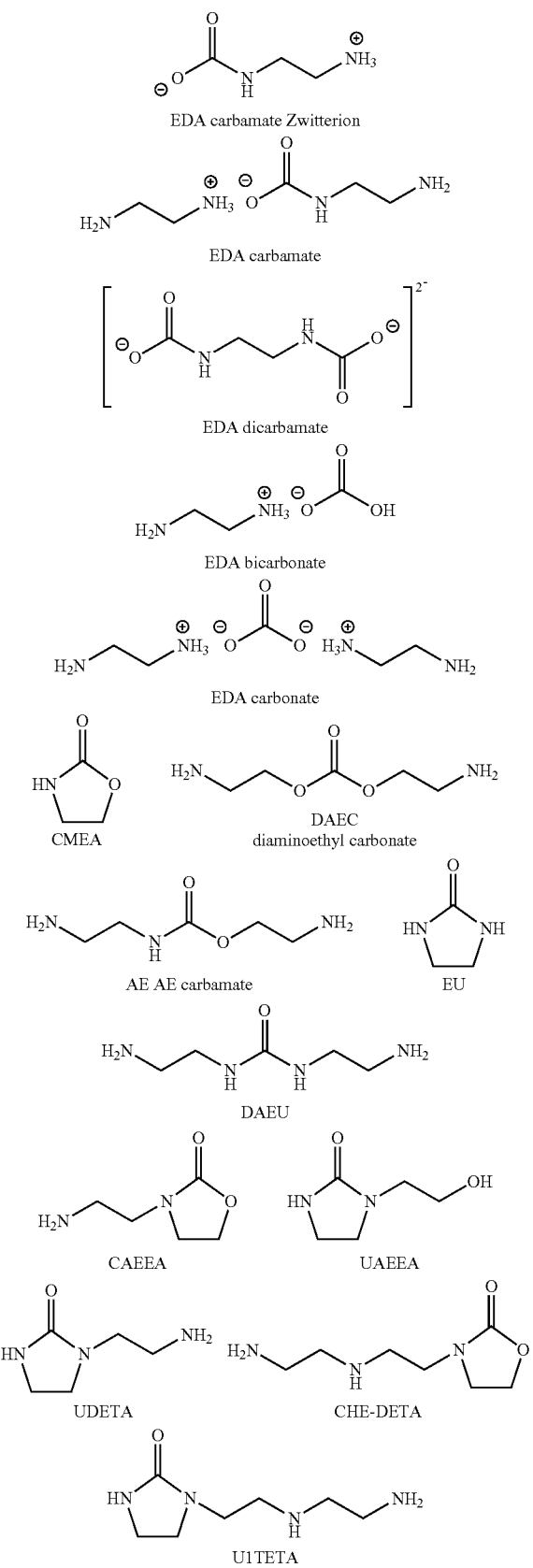

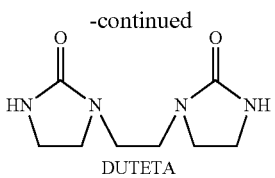

DUTETA

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal urea of triethylene tetramine, and DUTETA stands for the 1,3-diurea of triethylene tetramine.

It should be noted that compounds exist that contain more than one carbonyl group that can be released from the molecule, such as for example DU-TETA. When determining the molar ratio for such compounds there should be an adjustment for the molar amount of carbon oxide they can release to other molecules, such as for example to the ethanolamine-functional compound. Accordingly, 1 mole of DU-TETA should be considered 2 moles of carbon oxide delivering agent.

The carbon oxide delivering agent is most preferably added to the reaction in the form of carbon dioxide, urea or provided at least in part as one compound with the ethanolamine-functional compound and/or the amine-functional compound in the form of a CO adduct, e.g., an adduct comprising a cyclic ethylene urea unit

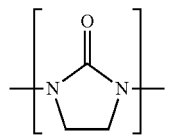

a carbamate unit

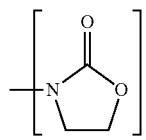

or a linear urea structure

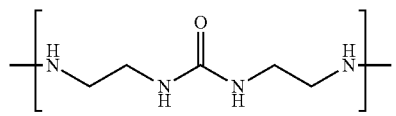

Heating a suitable mixture of an ethanolamine, an amine that is not tertiary and a carbon oxide delivering agent to a relatively high temperature provides a way to produce a higher amine and CO containing derivative like the above carbamate and urea compounds that can serve as a carbon oxide delivering agent.

If carbon dioxide is added to the amine-functional compound and/or ethanolamine-functional compound, as the carbon oxide delivering agent, water may be formed in the creation of a urea or carbamate. Hence a preferred embodiment of the process contains a preceding step wherein carbon dioxide is reacted with an ethanolamine-functional compound or an amine-functional compound and the carbon oxide delivering agent is present in the process at least partly as a cyclic or non-cyclic carbamate derivative of the ethanolamine-functional compound or as a cyclic or non-cyclic urea derivative of the amine-functional compound, or a combination of these, and even more preferred, a subsequent additional step is performed of removing water after the carbon dioxide has reacted with the ethanolamine-functional compound or the amine-functional compound. In this way the water balance before starting the process of the invention cannot only be adjusted as desired but during the process it can also be better controlled and therefore the process will lead to a more balanced conversion and selectivity, and hence improved yield.

Not only the reaction between carbon dioxide and either of the amine-functional compound or the ethanolamine-functional compound may result in the formation of water but another molecule of water may form when in the process of the present invention the amine functional compound and the ethanolamine-functional compound react in the presence of a carbon oxide delivering agent to give the higher ethylene amine compound.

It is preferred to remove or add water during the process of the invention, such as removing water that is formed during the process, to maintain the amount of water in the preferred range of 0.01-2 moles per mole of carbon oxide delivering agent. Water addition or removal can be done intermittently, semi continuously or continuously during the process. The water can be removed by evaporation, flashing, stripping, extraction, adsorption or other physical as well as chemical water scavenging techniques known to the person skilled in the art.

The amine-functional compound is a compound containing one or more amine groups, preferably at least two amine groups, and no alcohol groups.

In a further preferred embodiment in the process the ethanolamine-functional compound is of the formula OH—(C2H4-NH-)qH wherein q is at least 1 and the amine-functional compound is of the formula NH2-(C2H4-NH)rH wherein r is at least 1, wherein the sum of q+r is at least 3 and wherein optionally one or more q or r units may be present as a cyclic ethylene urea, or cyclic ethylene carbamate unit.

In another preferred embodiment the ethanolamine-functional compound and the carbon oxide delivering agent are at least partly added as one compound by using a carbamate adduct and/or the amine-functional compound and the carbon oxide delivering agent are at least partly added as one compound by using an urea adduct.

The amine-functional compound even more preferably comprises an amino-functional compound of the formula HN—(CH2-CH2-NH)r-H, wherein r is 1 to 10, more in particular 1 to 5, e.g., compounds selected from the group of ethylenediamine (EDA), diethylenetriamine (DETA), triethylenetetramine (TETA), tetraethylenepentamine (TEPA), and mixtures thereof.

In another preferred embodiment the ethanolamine-functional compound preferably comprises a ethanolamine-functional compound of the formula HO—(CH2-CH2-NH)q-H wherein q is 1 to 10, more in particular 1 to 5, e.g., compounds selected from the group of monoethanolamine (MEA), aminoethylethanolamine (AEEA) and hydroxyethyl diethylene triamine (HE-DETA).

In a more preferred embodiment the ethanolamine-functional compound is AEEA, UAEEA, CAEEA or a mixture thereof and the amine-functional compound EDA, EU, DETA, UDETA, or a mixture thereof, the ethanolamine-functional compound is MEA, CMEA or a mixture thereof and the amine-functional compound EDA, EU, DETA, UDETA, TETA, UTETA or a mixture thereof.

In an embodiment the amine-functional compound and/or the ethanolamine-functional compound are obtained directly or indirectly from an amine production process as described above, such as for example a reductive amination process or EDC process.

In a preferred embodiment the molar ratio of carbon oxide delivering agent:amine-functional compound is of from 0.1:1 to 10:1, preferably 0.5:1-3:1, even more preferably it is higher than 1:1 and up to 2.5:1.

The product mixture can be further processed or fractionated into several products that each independently are either pure compounds or mixture of compounds, some of which may be recycled.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process is preferably performed at a temperature of at least 100° C. The temperature should preferably be lower than 400° C. More preferably the temperature is between 200 and 360° C. Even more preferably the temperature is between 230 and 340° C. Most preferably the temperature is between 250 and 310° C. In embodiments where the ethanolamine-functional compound is monoethanolamine the most preferred temperature range is between 230 and 290° C.

The reaction time during the process is in an embodiment between 5 minutes and 15 hours, preferably between 0.5 and 10 hours, more preferably between 1 and 6 hours.

The process can be carried out in one or multiple batch reactors, possibly in fed-batch operation, and/or in a continuously operating system in one reactor or in a cascade of continuous flow reactors, optionally with multiple feeding points. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

The invention is illustrated by below Examples

In the Examples, for a reaction mixture containing a single ethanol amine and its urea/carbamate derivative in the starting mixture, a general selectivity has been calculated from:

$$\text{Selectivity} = \frac{\text{mol }(U)\text{ethylene amines formed}}{\text{mol }(U)\text{ethanolamine at start} - \text{mol }(U)\text{ethanolamine remaining}}$$

Here, (U)ethylene amine stands for ethylene amine and its terminal urea derivative and (U)ethanol amine stands for ethanol amine and its urea derivative or carbamate derivative in the case of CMEA. If the formed (U)ethylene amine can react further with a second ethanolamine equivalent then this can be reflected in the selectivity formula as exemplified below.

For example for the reaction mixture starting with AEEA, EDA and carbon oxide delivering agent, the selectivity is calculated from:

$$\text{Selectivity} = 100\% x \frac{\text{mol }(D)(U)\text{TETA formed}}{\text{mol }(U)\text{AEEA at start} - \text{mol }(U)\text{AEEA remaining}}$$

As another example for the reaction mixture starting with CMEA and EU to react to TETA, the selectivity is then calculated from:

$$\text{Selectivity} = 100\% x \frac{\text{mol }[(D)(U)\text{TETA formed}]x2 + \text{mol }(U)\text{DETA formed}}{\text{mol }(C)\text{MEA at start} - \text{mol }(C)\text{MEA remaining}}$$

Here, (D)(U)TETA stands for tri-ethylene tetra-amine and its terminal mono- and di-urea derivatives and (U)AEEA stands for amino ethyl ethanol amine and its urea derivative.

For a reaction mixture containing more than one ethanol amine and its urea derivative in the starting mixture, a general selectivity can be calculated from:

$$\text{Selectivity} = 100\% x \frac{\text{mol }(U)\text{EA formed} * \text{stoichiometric factor}}{\text{mol }(U)\text{ethanolamines at start} - \text{mol }(U)\text{ethanolamines remaining}}$$

With the ethanolamines and their urea derivatives exclusively the types that were initially present, and not any newly formed (higher) ethanol amines.

The conversion is calculated from:

$$\text{Conversion} = 100\% x \left(1 - \frac{\text{mol ethanolamines remaining}}{\text{mol ethanolamines at start}}\right)$$

Example 1: Investigation of the Effect of Water in a System Containing a CO:Amine Ratio of 2:1

To investigate the effect of water on conversion rate and selectivity UAEEA and EU were mixed in a 1:1 molar ratio. Then 0, 1, 2, 4 or 8 molar equivalents of water were added to the mixture. Each of these mixtures was loaded into a reactor vessel and heated to 280 deg C. for two hours resulting in the conversion of UAEEA and EU to a TETA product mixture that is defined as the combined fraction of L-TETA and its terminal urea derivatives. After two hours of reaction time, the reaction mixture was cooled down and analyzed using GC-FID, which stands for gas chromatography using a flame ionization detector.

From the experimental results shown in Table 1 it becomes clear that the conversion level after two hours of reaction time at the same reaction temperature increases with an increase in water content. The addition of 1 molar equivalent of water (which corresponds with 0.5 molar equivalent of water on urea units in the system) to a mixture of UAEEA and EU results in an increase in conversion from 16% to 46%.

In addition to its effect on conversion, water also affects the selectivity of the process in these systems. A higher water concentration results in the formation of more byproducts and hence lower selectivity. The addition of 1 molar equivalent of water to a mixture of UAEEA and EU results in a decrease of selectivity from 100% to 53%.

The best balance between conversion and selectivity is achieved in the area between 0 and 2 molar equivalent of water on the molar amount of urea units in the system.

TABLE 1

| # | Starting mixture | Reaction time (hr) | Temp. (C.) | $H_2O/CO$ (mol/mol) | Conv.[1] | Select.[2] |
|---|---|---|---|---|---|---|
| 1A* | 1 UAEEA + 1EU | 2 | 280 | 0 | 16% | 100% |
| 1B | 1 UAEEA + 1 EU + 1 $H_2O$ | 2 | 280 | 0.5 | 46% | 53% |
| 1C | 1 UAEEA + 1 EU + 2 $H_2O$ | 2 | 280 | 1 | 76% | 26% |
| 1D | 1 UAEEA + 1 EU + 4 $H_2O$ | 2 | 280 | 2 | 89% | 17% |
| 1E* | 1 UAEEA + 1 EU + 8 $H_2O$ | 2 | 280 | 4 | 86% | 16% |

[1]Conversion is determined as indicated above.
[2]Selectivity is determined as indicated above.
*Examples 1A and 1E are comparative Examples Example 2: Investigation of the Effect of Water in a System Containing a CO:Amine Ratio of 1:1

To investigate the effect of water on conversion rate and selectivity AEEA and EU were mixed in a 1:1 molar ratio. Then 0, 1, or 4 molar equivalents of water were added to the mixture. Each of these mixtures was then loaded into a reactor vessel and heated to 280 deg C. for two hours resulting in the conversion of AEEA and EU to a TETA product mixture as defined in Example 1. After two hours of reaction time, the reaction mixture was cooled down and analyzed using GC-FID, which stands for gas chromatography using a flame ionization detector.

From the experimental results shown in Table 2 it becomes clear that the finding that conversion increases at a higher H2O level until ratio H2O/CO=2, yet selectivity decreases, is confirmed also by this Example. The addition of 1 molar equivalent of water to a mixture of AEEA and EU results in a significant increase in conversion from 35% to 58%. The addition of 4 molar equivalents of water to the reaction mixture results in a very minimal increase in the conversion from 58 to 59%, but selectivity further drops.

TABLE 2

| # | Starting mixture | Reaction time (hr) | Temp. (C.) | $H_2O/CO$ (mol/mol) | Conv. | Select. |
|---|---|---|---|---|---|---|
| 2.A* | 1 AEEA + 1 EU | 2 | 280 | 0 | 35% | 71% |
| 2.B | 1 AEEA + 1 EU + 1 $H_2O$ | 2 | 280 | 1 | 58% | 31% |
| 2.C* | 1 AEEA + 1 EU + 4 $H_2O$ | 2 | 280 | 4 | 59% | 28% |

* Examples 2A and 2C are comparative

Example 3: Investigation of the Effect of Water on Selectivity in a System Containing a CO:Amine Ratio of 2.7:2 (1.35:1)

To investigate the effect of water on selectivity UAEEA, EU and EDA were mixed in a 1:1.7:0.3 molar ratio. Then 1, and 4 molar equivalents of water were added to the mixture, because of the 2.7 equivalent of urea units resulting in a water:carbon oxide delivering agent of respectively 0.37:1 and 1.48:1. Each of these mixtures was then loaded into a reactor vessel and heated to 270 deg C. for two hours resulting in the conversion of UAEEA and EDA to a TETA product mixture. After two hours of reaction time, the reaction mixture was cooled down and analyzed using GC-FID, which stands for gas chromatography using a flame ionization detector.

From the experiments in Table 3 it becomes clear that a good balance between conversion and selectivity is achieved performing the process with the right molar amount of water.

TABLE 3

| # | Starting mixture | Reaction time (hr) | Temp. (C.) | $H_2O/CO$ (mol/mol) | Conv. | Select. |
|---|---|---|---|---|---|---|
| 3.A | 1 UAEEA + 1.7 EU + 0.3 EDA + 1 $H_2O$ | 5 | 270 | 0.37 | 91% | 48% |
| 3.B | 1 UAEEA + 1.7 EU + 0.3 EDA + 4 $H_2O$ | 5 | 270 | 1.48 | 96% | 33% |

Example 4: Investigation of the Effect of Water in a System with CMEA and EU as Raw Materials in a Process to Prepare TETA To investigate the effect of water on yield CMEA and EU were mixed in a 1:1 molar ratio. Then 0.008, 0.15, 0.5, 1, 2, 4 or 8 molar equivalents of water were added to the mixture. Each of these mixtures was loaded into a reactor vessel and heated to 250 deg C. for two hours resulting in the conversion of CMEA and EU to a TETA product mixture, that is defined as the combined fraction of L-TETA and its terminal urea derivatives. After two hours of reaction time, the reaction mixture was cooled down and analyzed using GC-FID, which stands for gas chromatography using a flame ionization detector.

From the experimental results shown in Table 4 it becomes clear that the highest yield, 0.87 mol/kg, was obtained for the system containing 0.5 mol H2O per mol CO (though it might be possible that a higher yield will be found at another point in the range between 0.07 and 1 mol H2O per mol of CO if more ratios will be measured). Adding small amounts of water to the reaction mixture promotes the yield but increasing $H_2O$ levels too much was found to have a detrimental effect on yield.

TABLE 4

| # | Starting mixture | Reaction time (hr) | Temp. (° C.) | $H_2O/CO$ (mol/mol) | Yield (mol/kg) | Relative yield[1] |
|---|---|---|---|---|---|---|
| 4A | 1 CMEA + 1 EU + 0.008 $H_2O$ | 2 | 250 | 0.004 | 0.2 | 26% |
| 4B | 1 CMEA + 1 EU + 0.15 $H_2O$ | 2 | 250 | 0.07 | 0.79 | 92% |
| 4C | 1 CMEA + 1 EU + 1 $H_2O$ | 2 | 250 | 0.5 | 0.87 | 100% |

TABLE 4-continued

| # | Starting mixture | Reaction time (hr) | Temp. (°C.) | $H_2O/CO$ (mol/mol) | Yield (mol/kg) | Relative yield[1] |
|---|---|---|---|---|---|---|
| 4D | 1 CMEA + 1 EU + 2 $H_2O$ | 2 | 250 | 1 | 0.72 | 83% |
| 4E | 1 CMEA + 1 EU + 4 $H_2O$ | 2 | 250 | 2 | 0.51 | 59% |
| 4F | 1 CMEA + 1 EU + 8 $H_2O$ | 2 | 250 | 4 | 0.34 | 39% |

[1]Relative yield represents the ratio of the yield obtained and the yield obtained at the optimal water level, in this case H2O/CO = 0.5, multiplied by 100%.

Urea groups were successfully removed from the cyclic urea products in the mixture formed in example 4C by a subsequent addition of a 2M aqueous NaOH solution and heating the mixture to a temperature of 200° C.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process to prepare ethylene amines of the formula $NH_2-(C_2H_4-NH-)_pH$ wherein p is at least 2, or derivatives thereof wherein one or more units $-NH-C_2H_4-NH$ are present as a cyclic ethylene urea unit

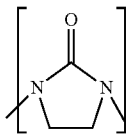

comprising:
reacting an ethanolamine-functional compound $OH-(C_2H_4-NH-)_qH$ or $HO-(C_2H_4-NH)_q-C_2H_4-OH$ wherein q is at least 1, and an amine-functional compound $NH_2-(C_2H_4-NH-)_{rH}$ wherein r is at least 1, in the presence of a carbon oxide delivering agent and water, with a molar ratio of water:carbon oxide delivering agent of from about 0.01:1 to about 2:1.

2. The process of claim 1 wherein the molar ratio of water:carbon oxide delivering agent is from about 0.05:1 to about 1:1.

3. The process of claim 1, where the carbon oxide delivering agent is carbon dioxide, urea or provided at least in part as one compound with the ethanolamine-functional compound and/or the amine-functional compound in the form of a CO adduct.

4. The process of claim 1 further comprising reacting carbon dioxide with an ethanolamine-functional compound or an amine-functional compound and the carbon oxide delivering agent is present in the process at least partly as a cyclic or non-cyclic carbamate derivative of the ethanolamine-functional compound or as a cyclic or non-cyclic urea derivative of the amine-functional compound, or a combination of these.

5. The process of claim 1 further comprising removing water after the carbon dioxide has reacted with the ethanolamine-functional compound or the amine-functional compound.

6. The process of claim 1 further comprising adding or removing water during the process intermittently, semi-continuously or continuously to maintain the amount of water such that the molar ratio of water:carbon oxide delivering agent remains from 0.01:1 to 2:1.

7. The process of claim 1 wherein the molar ratio of carbon oxide delivering agent:amine-functional compound is from about 0.1:1 to about 10:1.

8. The process of claim 1, wherein the amine-functional compound comprises an amino-functional compound of the formula $HN-(CH_2-CH_2-NH)_r-H$, wherein r is 1 to 10.

9. The process of claim 1, wherein the ethanolamine-functional compound comprises a ethanolamine-functional compound of the formula $HO-(CH_2-CH_2-NH)_q-H$ wherein q is 1 to 10.

10. The process of claim 1 further comprising subjecting the reaction product comprising one or more compounds in the form of urea adducts to a CO removal reaction to convert the urea adduct into amine compounds.

11. The process of claim 3, wherein the CO adduct comprises a cyclic ethylene urea unit

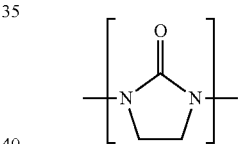

a carbamate unit

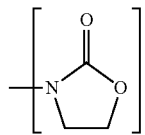

or a linear urea structure

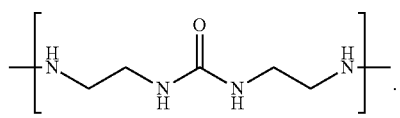

* * * * *